(12) United States Patent
Cahoon

(10) Patent No.: US 7,002,060 B1
(45) Date of Patent: Feb. 21, 2006

(54) ENZYMES INVOLVED IN PETROSELINIC ACID BIOSYNTHESIS

(75) Inventor: Edgar B. Cahoon, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/732,597

(22) Filed: Dec. 8, 2000

Related U.S. Application Data

(60) Provisional application No. 60/169,968, filed on Dec. 9, 1999.

(51) Int. Cl.
*A01H 5/00* (2006.01)
*C12N 5/04* (2006.01)
*C12N 15/82* (2006.01)

(52) U.S. Cl. ............. 800/298; 800/281; 435/69.1; 435/320.1; 435/419; 536/23.2; 536/23.6

(58) Field of Classification Search ............. 536/23.6, 536/23.2; 435/69.1, 320.1, 419, 252.3, 468; 800/281, 298
See application file for complete search history.

(56) References Cited

OTHER PUBLICATIONS

Van de Loo et al, PNAS, USA, vol. 92:6743-6747, Jul. 1995.*
Broun et al, Science 282: 131-133, Nov. 13, 1998.*
De Luca, V., AgBiotech News and Information 5 (6): 225N-229N, 1993.*
Doerks et al, TIG 14 (6):248-250, 1998.*
Smith et al, Nature Biotechnology 15: 1222-1223, Nov. 15, 1997.*
Brenner, SE, TIG 15 (4): 132-133, Apr. 1999.*
Bork, P, TIG 12 (10): 425-427, Oct. 1996.*
Fred H. Mattson et al., Journ. of Lipid Res., vol. 26:194-202, 1985, Comparison of Effects of Dietary Saturated, Monounsaturated, and Polyunsaturated Fatty Acids on Plasma Lipids and Lipoproteins in Man.
Edgar B. Cahoon et al., PNAS, vol. 89:11184-11188, Dec. 1992, Expression of a Coriander Desaturase Results in Petroselinic Acid Production in Transgenic Tobacco.
Mi Chung Suh et al., Plant J., vol. 17(6):679-688, 1999, Isoforms of Acyl Carrier Protein Involved in Seed-Specific Fatty Acid Synthesis.
John Shanklin et al., Annu. Rev. Plant Physiol. Plant Mol. Biol., vol. 49:611-641, 1998, Desaturation and Related Modifications of Fatty Acids.
Edgar B. Cahoon et al., PNAS, vol. 94:4872-4877, May 1997, Redesign of Soluble Fatty Acid Desaturases from Plants for Altered Substrate Specificity and Double Bond Position.
National Center for Biotechnology Information General Identifier No. 417819, May 30, 2000, Cahoon, E.B. et al., Expression of a Coriander Desaturase Results in Petroselinic Acid Production in Transgenic Tobacco.
National Center for Biotechnology Information General Identifier No. 5669599, Aug. 2, 1999, Suh, M.C. et al.

* cited by examiner

*Primary Examiner*—Elizabeth F. McElwain
(74) *Attorney, Agent, or Firm*—Morgan & Finnegan, L.L.P.

(57) ABSTRACT

This invention relates to an isolated nucleic acid fragment encoding a gene involved in petroselinic acid biosynthesis. The invention also relates to the construction of a chimeric gene encoding all or a portion of the gene involved in petroselinic acid biosynthesis, in sense or antisense orientation, wherein expression of the chimeric gene results in production of altered levels of the gene involved in petroselinic acid biosynthesis in a transformed host cell.

15 Claims, 1 Drawing Sheet

FIGURE 1: Alignment of Delta-4 16:0 Desaturases From English Ivy (SEQ ID NO:2) and Coriander (gi 417819)

```
SEQ ID 2    MALKLN----FQCKKNHPAAFAKSPLPVTRVSSPRVFMASTVNSNSMVLDNLKSPPNLQVTHSMPPQKLEIFKSLDDWARNNVLIHLKSV
417819      MAMKLNALMTLQCPKRN--MFTRIAPPQAGRVRSKVSMASTLHASPLVFDKLKAGR--------PEVDELFNSLEGWARDNILVHLKSV

SEQ ID 2    EKSWQPQDYLPDPVSDGFEEQVRELRERAKEIPDDYFVVLVGDMITEEALPTYMSMLNRCDGIKDETGAEPSAWAMWTRAWTAEENRHGD
417819      ENSWQPQDYLPDPTSDAFEDQVKEMRERAKDIPDEYFVVLVGDMITEEALPTYMSMLNRCDGIKDDTGAQPTSWATWTRAWTAEENRHGD

SEQ ID 2    LLNKYLYLSGRVDMRKIEKTIQYLIGSGMDIKSENSPYLGFIYTSFQERATFISHANTAKLAQHYGDKNLAHICGSIASDEKRHATAYTK
417819      LLNKYLYLSGRVDMRMIEKTIQYLIGSGMDTKTENCPYMGFIYTSFQERATFISHANTAKLAQHYGDKNLAQVCGNIASDEKRHATAYTK

SEQ ID 2    IVEKLAEIDPDTTVIAFADMRKKITMPAHLMYDGSDELLFKHFTAVAQRVGVYSALDYCDILEFLVDKWNVERLTGLSDEGRKAQEYVC
417819      IVEKLAEIDPDTTVIAFSDMRKKIQMPAHAMYDGSDDMLFKHFTAVAQQIGVYSAWDYCDIIDFLVDKWNVAKMTGLSGEGRKAQEYVC

SEQ ID 2    ELGPKIRRVEEKVQGKEKKKAEHPVSFSWIFNRELKI
417819      SLAAKIRRVEEKVQGKEKK--AVLPVAFSWIFNRQIII
```

Figure 2: Alignment of Acyl Carrier Proteins From English Ivy (SEQ ID NOs:4 and 6) and Coriander (gi 5669599)

```
SEQ ID 4    MASVTASSISFTSIASSLKQNOGLAKSSISLSVNGKSFRSLRLLSAPLRFRVSCAAKPATVDKVCEIVRKQLALPLILQVTGESKFAALG
SEQ ID 6    MASVTASSISFTSIASSLKQNOGLAKSSISLSVNGKSFRSLRLLSAPLRFRVSCAAKPATVDKVCEIVRKQLALPADSAVTGESKFAALG
5669599     MAAFTASSVSFTPLSISLNQTKGFARGSVSIPAKAKSFGALTLRNAPLRFRVSCAAKPETVEKVCEIVKKQLALPPTTEVSGDSKFAALG

SEQ ID 4    ADSLDTVEIVMGLKEEFGIKRG-------------KK
SEQ ID 6    ADSLDTVEIVMGLEEEFGISVEEESAQTIATVQDAADLIEKLVEKKE
5669599     ADSLDTVEIVMGLEEEFGISVEEESAQAIATVQDAADLIEKLCEKKE
```

ENZYMES INVOLVED IN PETROSELINIC ACID BIOSYNTHESIS

This application claims the benefit of U.S. Provisional Application No. 60/169,968, filed Dec. 9, 1999.

FIELD OF THE INVENTION

This invention is in the field of plant molecular biology. More specifically, this invention pertains to nucleic acid fragments encoding genes involved in petroselinic acid biosynthesis in plants and seeds.

BACKGROUND OF THE INVENTION

Monounsaturated fatty acids are important components of human nutrition and have been found to have health benefits, such as lowering the risk of heart disease by reducing the "bad" (low-density lipoprotein) cholesterol while maintaining the "good" (high-density lipoprotein) cholesterol (Mattson et al. (1985) *Journal of Lipid Research* 26:194–202). The most common naturally occurring monounsaturated fatty acid is oleic acid ($18:1\Delta^9$), which is found in abundance in "healthy" oils such as olive and canola. Therefore, it is desirable to produce oils that have increased ratios of monounsaturated to polyunsaturated fatty acids such as linoleic or linolenic acids (18:2, and 18:3, respectively), and the unsaturated fatty acids such as palmitic and stearic (16:0, and 18:0, respectively). Petroselinic acid ($18:1\Delta^6$) is a monounsaturated fatty acid that differs from the more common oleic acid by the position of the double bond in the hydrocarbon chain. It is believed that petroselinic acid is made via a pathway wherein acyl carrier protein (ACP)-bound palmitic acid (16:0) is converted to hexadecenoic acid ($16:1\Delta^4$) by the enzyme $\Delta^4$-16:0-acyl carrier protein desaturase ($\Delta^4$-16:0-ACP desaturase) (Cahoon et al. (1992) *Proc Natl Acad Sci* 89:11184–11188). The hexadecenoic acid is then elongated to form petroselinic acid by a β-keto-acyl-ACP synthase (KASII). Introduction of a coriander $\Delta^4$-16:0-acyl carrier protein desaturase into transgenic tobacco resulted in production of both petroselinic acid and hexadecenoic acid, neither of which is normally found in tobacco (Cahoon et al. (1992) *Proc Natl Acad Sci* 89:11184–11188). It is believed that specialized isoforms of ACP may be involved in this pathway which may facilitate the accumulation of petroselinic acid versus hexadecenoic acid (Suh et al. (1999) *Plant J* 17:679–688). Thus, it is possible to direct the accumulation of novel monounsaturated fatty acids in higher plants.

Another important product of this pathway comes from the breakdown products of the petroselinic acid and hexadecenoic acid. Chemical cleavage of the double bonds in these oils will release 12-carbon lauric acid, a component of detergents and surfactants. The other product of the cleavage of petroselinic acid is the 6-carbon adipic acid which is a monomeric component of nylon 66. Fatty acids such as petroselinic can also serve as substrates for epoxidases, hydroxylases, and other modifying activities that will produce novel products.

In a sixth embodiment, the invention also relates to a process for producing an isolated host cell comprising a chimeric gene of the present invention or an isolated polynucleotide of the present invention, the process comprising either transforming or transfecting an isolated suitable host cell with a chimeric gene or isolated polynucleotide of the present invention.

In a seventh embodiment, the invention concerns a $\Delta^4$-16:0-ACP desaturase polypeptide of at least 361 amino acids having at least 75% identity based on the Clustal method of alignment compared to a polypeptide selected from SEQ ID NO:2, and an ACP isoform polypeptide of at least 114 amino acids comprising at least 75% identity based on the Clustal method of alignment compared to a polypeptide selected from the group consisting of SEQ ID NOs:4, and 6.

In an eighth embodiment, the invention relates to a method of selecting an isolated polynucleotide that affects the level of expression of a $\Delta^4$-16:0-ACP desaturase and an ACP isoform polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the $\Delta^4$-16:0-ACP desaturase and an ACP isoform polypeptide or enzyme activity in the host cell containing the isolated polynucleotide; and (d) comparing the level of the $\Delta^4$-16:0-ACP desaturase and an ACP isoform polypeptide or enzyme activity in the host cell containing the isolated polynucleotide with the level of the $\Delta^4$-16:0-ACP desaturase and an ACP isoform polypeptide or enzyme activity in the host cell that does not contain the isolated polynucleotide.

In a ninth embodiment, the invention concerns a method of obtaining a nucleic acid fragment encoding a substantial portion of a $\Delta^4$-16:0-ACP desaturase and an ACP isoform polypeptide, preferably a plant $\Delta^4$-16:0-ACP desaturase and an ACP isoform polypeptide, comprising the steps of: synthesizing an oligonucleotide primer comprising a nucleotide sequence of at least 300 (preferably at least 400; most preferably at least 600) contiguous nucleotides derived from a nucleotide sequence selected from the group consisting of SEQ ID NOs:1, 3, and 5, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a $\Delta^4$-16:0-ACP desaturase and an ACP isoform amino acid sequence.

In a tenth embodiment, this invention relates to a method of obtaining a nucleic acid fragment encoding all or a substantial portion of the amino acid sequence encoding a $\Delta^4$-16:0-ACP desaturase and an ACP isoform polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the $\Delta^4$-16:0-ACP desaturase and an ACP isoform polynucleotide in an amount sufficient to complement a null mutant to provide a positive selection means.

In a thirteenth embodiment, this invention relates to a method of altering the level of expression of genes involved in petroselinic acid biosynthesis in a host cell comprising: (a) transforming a host cell with a chimeric gene of the present invention; and (b) growing the transformed host cell under conditions that are suitable for expression of the chimeric gene wherein expression of the chimeric gene results in production of altered levels of the genes involved in petroselinic acid biosynthesis in the transformed host cell.

In a fourteenth embodiment, this invention concerns a method for producing petroselinic acid in a plant which comprises: (a) transforming a plant with a chimeric gene comprising an isolated nucleic acid fragment encoding a plant fatty acid modifying enzyme associated with the production of petroselinic acid wherein said nucleic acid fragment encoding a polypeptide that is at least 75% identical to a polypeptide encoded by any of the nucleotide sequences set forth in SEQ ID NOs: 1 or 5, or a functionally equivalent subfragment thereof or a complement thereof operably linked to suitable regulatory sequences; (b) growing the transformed plant under conditions suitable for the expression of the chimeric gene; and (c) selecting those transformed plants producing petroselinic acid.

In fifteenth embodiment, this invention concerns a method for producing seed oil containing fatty acids having petroselinic acid in the seeds of plants which comprises: (a) transforming a plant with a chimeric gene comprising an isolated nucleic acid fragment encoding a plant fatty acid modifying enzyme associated with the production of petroselinic acid wherein said nucleic acid fragment encoding a polypeptide that is at least 75% identical to a polypeptide encoded by any of the nucleotide sequences set forth in SEQ ID NOs: 1 or 5, or a functionally equivalent subfragment thereof or a complement thereof operably linked to suitable regulatory sequences; (b) growing a fertile mature plant from the transformed plant cell of step (a); (c) screening progeny seeds from the fertile plants of step (b) for altered levels of petroselinic acid; and (d) processing the progeny seed of step (c) to obtain seed oil containing petroselinic acid.

BRIEF DESCRIPTION OF THE DRAWINGS AND SEQUENCE LISTINGS

The invention can be more fully understood from the following detailed description and the accompanying drawings and Sequence Listing which form a part of this application.

FIG. 1 shows a comparison of the amino acid sequence of the English ivy $\Delta^4$-16:0-ACP desaturase (SEQ ID NO:2) to the $\Delta^4$-16:0-ACP desaturase polypeptide from coriander (SEQ ID NO:7).

FIG. 2 shows a comparison of the amino acid sequences of the English ivy ACP (SEQ ID NO:4 and 6) to the diverged ACP isoform from coriander (SEQ ID NO:8).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Enzymes Involved in Petroselinic Acid Biosynthesis

| Protein | Clone Designation | SEQ ID NO: (nucleotide) | SEQ ID NO: (amino acid) |
|---|---|---|---|
| $\Delta^4$-16:0-ACP desaturase (English Ivy) | ehh1c.pk002.f22 | 1 | 2 |
| Acyl Carrier Protein (English Ivy) | ehh1c.pk001.k9 | 3 | 4 |
| Acyl Carrier Protein (English Ivy) | ehh1c.pk001.k9:fis | 5 | 6 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the requirements of 37 C.F.R. §1.822.

DETAILED DESCRIPTION OF THE INVENTION

"Petroselinic acid" (18:1$\Delta^6$) is a monounsaturated fatty acid that differs from the more common oleic acid by the position of the double bond in the hydrocarbon chain. It is believed that petroselinic acid is made via a pathway wherein acyl carrier protein (ACP) bound palmitic acid (16:0) is converted to hexadecenoic acid (16:1$\Delta^4$) by the enzyme $\Delta^4$-16:0-acyl carrier protein desaturase ($\Delta^4$-16:0-ACP desaturase) (Cahoon et al. (1992) *Proc Natl Acad Sci* 89:11184–11188). The hexadecenoic acid is then elongated to form petroselinic acid by a β-keto-acyl-ACP synthase (KASII). Introduction of a coriander $\Delta^4$-16:0-acyl carrier protein desaturase into transgenic tobacco resulted in production of both petroselinic acid and hexadecenoic acid, neither of which is normally found in tobacco (Cahoon et al. (1992) *Proc Natl Acad Sci* 89:11184–11188. It is believed that specialized isoforms of ACP may be involved in this pathway which may facilitate the accumulation of petroselinic acid versus hexadecenoic acid (Suh et al. (1999) *Plant J* 17:679–688). Thus, it is possible to direct the accumulation of novel monounsaturated fatty acids in higher plants.

The term "$\Delta^4$-" (delta-4) refers to a position of a fatty acid chain. For an 16-carbon fatty acid chain (such as palmitic acid) the terms "$\omega^{12}$" and "$\Delta^4$" are equivalent since ω-carbons are counted from the methyl end while Δ-carbons are counted from the carboxyl end. Double bonds are referred to as "cis" or "trans" because they are chiral units that can assume the following non-equivalent structures:

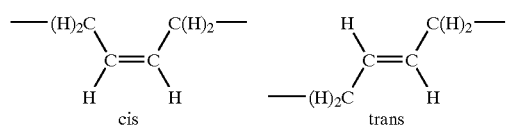

In the context of this disclosure, a number of terms shall be utilized. The terms "polynucleotide," "polynucleotide sequence," "nucleic acid sequence," and "nucleic acid fragment"/"isolated nucleic acid fragment" are used interchangeably. These terms encompass nucleotide sequences and the like. A polynucleotide may be an RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 300 contiguous nucleotides, preferably at least 400 contiguous nucleotides, most preferably at least 600 contiguous nucleotides derived from SEQ ID NOs:1, 3, and 5, or the complement of such sequences.

The term "isolated" refers to materials, such as nucleic acid molecules and/or proteins, which are substantially free from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping sequences. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence, to form a "contig".

As used herein, "substantially similar," in the case of nucleic acid fragments, refers to changes in one or more nucleotide bases that result in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to alter gene expression patterns by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

In one embodiment, substantially similar nucleic acid fragments may be obtained by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 300 (preferably at least 400, most preferably at least 600) contiguous nucleotides derived from a nucleotide sequence selected from the group consisting of SEQ ID NOs:1, 3, and 5, and the complement of such nucleotide sequences may be used in methods of selecting an isolated polynucleotide that affects the expression of a $\Delta^4$-16:0-ACP desaturase and an ACP isoform polypeptide in a host cell. A method of selecting an isolated polynucleotide that affects the level of expression of a polypeptide in a virus or in a host cell (eukaryotic, such as a plant cell or a yeast cell, or prokaryotic such as a bacterial cell) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art.

Suitable nucleic acid fragments (isolated polynucleotides of the present invention) encode polypeptides that are at least about 70% identical, preferably at least about 75%, more preferably at least about 80%, more preferably at least about 85%, still more preferably at least about 90%, and most preferably at least about 95% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein.

Suitable nucleic acid fragments not only have the above identities but typically encode a polypeptide having at least 10, preferably 20, more preferably 30, still more preferably 50, more preferably at least 100, more preferably at least 114 amino acids, more preferably at least 137 amino acids, more preferably at least 150 amino acids, preferably at least 200 amino acids, more preferably at least 250 amino acids, still more preferably at least 300 amino acids, more preferably at least 350 amino acids, more preferably at least 361 amino acids, and most preferably at least 394 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based-sequence comparison and identification tools that employ algorithms such as BLAST (Basic Local Alignment Search Tool; Altschul et al. (1993) *J. Mol. Biol.* 215:403410[; see also www.ncbi.nlm.nih.gov/BLAST/]). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer.

Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3'non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression"; as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) first nucleotide sequence encoding a polypeptide of at least 361 amino acids having at least 75% identity based on the Clustal method of alignment when compared to a polypeptide selected from SEQ ID NO:2, and (b) a a second nucleotide sequence encoding a polypeptide of at least 114 amino acids having at least 75% identity based on the Clustal method of alignment when compared to a polypeptide selected from the group consisting of SEQ ID NOs:4, and 6, or (c) a third and fourth nucleotide sequence comprising the complement of the first two nucleotide sequences.

Preferably, the first nucleotide sequence comprises a nucleic acid sequence selected from the group consisting of SEQ ID NOs: 1, 3, and 5, that codes for the polypeptide selected from the group consisting of SEQ ID NOs:2, 4, and 6.

Nucleic acid fragments encoding at least a portion of several gene involved in petroselinic acid biosynthesis have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other $\Delta^4$-16:0-ACP desaturase and an ACP isoform, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably one of at least 40, most preferably at least 60) contiguous nucleotides derived from a nucleotide sequence selected from the group consisting of SEQ ID NOs: 1, 3, and 5 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a $\Delta^4$-16:0-ACP desaturase and an ACP isoform polypeptide, preferably a substantial portion of a plant $\Delta^4$-16:0-ACP desaturase and an ACP isoform polypeptide, comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NOs: 1, 3, and 5, and the complement of such nucleotide sequences; and amplifying a nucleic acid fragment (preferably a cDNA inserted in a cloning vector) using the oligonucleotide primer. The amplified nucleic acid fragment preferably will encode a portion of a $\Delta^4$-16:0-ACP desaturase and an ACP isoform polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, a yeast cell, a bacterial cell, and a plant cell.

As was noted above, the nucleic acid fragments of the instant invention may be used to create transgenic plants in which the disclosed polypeptides are overexpressed, or their expression is suppressed, in various cell types or developmental stages. This would have the effect of altering the level of fatty acids with unusual modifications in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Noncoding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The skilled artisan readily recognizes that the choice of plasmid vector is dependent upon many factors, such as whether the vector is for protein expression, gene-overexpression or suppression, and in what type of host cell the vectors are propagated. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) EMBO J. 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may conter agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 361 amino acids having at least 75% identity based on the Clustal method of alignment when compared to a polypeptide selected from SEQ ID NO:2, and (b) a a second nucleotide sequence encoding a polypeptide of at least 114 amino acids having at least 75% identity based on the Clustal method of alignment when compared to a polypeptide selected from the group consisting of SEQ ID NOs:4, and 6.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded gene involved in petroselinic acid biosynthesis. An example of a vector for high level expression of the instant polypeptides in a bacterial host is provided (Example 7).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) Genomics 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) Am. J. Hum. Genet. 32:314–331).

The production and use of plant gene-derived probes for use in genetic mapping is described in Bernatzky and Tanksley (1986) Plant Mol. Biol. Reporter 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

In still a further aspect, this invention concerns a method for producing petroselinic acid in a plant which comprises:
  (a) transforming a plant with a chimeric gene comprising an isolated nucleic acid fragment encoding a plant fatty acid modifying enzyme associated with the production of petroselinic acid wherein said nucleic acid fragment encoding a polypeptide that is at least 75% identical to a polypeptide encoded by any of the nucleotide sequences set forth in SEQ ID NOs: 1 or 5, or a functionally equivalent subfragment thereof or a complement thereof operably linked to suitable regulatory sequences;

(b) growing the transformed plant under conditions suitable for the expression of the chimeric gene; and (c) selecting those transformed plants producing petroselinic acid.

In still a further aspect, this invention concerns a method for producing seed oil containing fatty acids having petroselinic acid in the seeds of plants which comprises:

(a) transforming a plant with a chimeric gene comprising an isolated nucleic acid fragment encoding a plant fatty acid modifying enzyme associated with the production of petroselinic acid wherein said nucleic acid fragment encoding a polypeptide that is at least 75% identical to a polypeptide encoded by any of the nucleotide sequences set forth in SEQ ID NOs: 1 or 5, or a functionally equivalent subfragment thereof or a complement thereof operably linked to suitable regulatory sequences;

(b) growing a fertile mature plant from the transformed plant cell of step (a);

(c) screening progeny seeds from the fertile plants of step (b) for altered levels of petroselinic acid; and (d) processing the progeny seed of step (c) to obtain seed oil containing petroselinic acid.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries: Isolation and Sequencing of cDNA Clones cDNA libraries representing mRNAs from English ivy tissues were prepared. The characteristics of the libraries are described below.

TABLE 2 cDNA Libraries from English Ivy (*Hedera helix*)

| Library | Tissue | Clones |
|---|---|---|
| ehh1c | English Ivy (*Hedera helix*) developing seed | ehh1c.pk002.f22, ehh1c.pk001.k9, ehh1c.pk001.k9:fis | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversior, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding genes involved in petroselinic acid biosynthesis were identified by conducting BLAST (Basic Local Alignment Search Tool; Altschul et al. (1993) *J. Mol. Biol.* 215:403410[; see also www.ncbi.nlm.nih.gov/BLAST/]) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding an English Ivy $\Delta^4$-16:0-ACP Desaturase The BLASTX search using the EST sequences from clones listed in Table 3 revealed similarity of the polypeptides encoded by the cDNAs to $\Delta^4$-16:0-ACP desaturase from *Coriandrum sativum* (NCBI General Identifier No. 417819). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to $\Delta^4$-16:0-ACP Desaturase

| Clone | Status | BLAST pLog Score [gi 417819] |
|---|---|---|
| ehh1c.pk002.f22 | Contig of PCR fragments | 171.0 |

FIG. 1 presents an alignment of the amino acid sequences set forth in SEQ ID NO:2 and the *Coriandrum* sequence (SEQ ID NO:7). The data in Table 4 represents a calculation of the percent identity of the amino acid sequences set forth in SEQ ID NO:2 and the *Coriandrum* sequence (SEQ ID NO:7). Full insert sequence of clone ehh1c.pk002.f22:fis (SEQ ID NO:9) confirmed the sequence presented in SEQ ID NO:1 with the addition of some 5'-end sequence, and the resolution of nucleotide 997 in SEQ ID NO:1, which is a "G" the converts the amino acid 317 of SEQ ID NO:2 to a glycine. The translation of SEQ ID NO:9 is shown in SEQ ID NO:10 which is identical to SEQ ID NO:2 except for the previously mentioned glycine at position 317. The 5'-untranslated leader to ehh1c.pk002.f22:fis has a 31 amino acid in frame extension to the coding region (LFLSLPCRIN-PVEITKSNQKIKIKTQEEEEE).

TABLE 4

Percent Identity of Amino Acid Sequences Deduced From the Nucleotide Sequences of cDNA Clones Encoding Polypeptides Homologous to $\Delta^4$-16:0-ACP Desaturase

| SEQ ID NO. | Percent Identity to [gi 417819] |
|---|---|
| 2 | 73.8% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE-1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a $\Delta^4$-16:0-ACP desaturase. These sequences represent the first English ivy sequence encoding a $\Delta^4$-16:0-ACP desaturase known to Applicant.

Example 4

Characterization of cDNA Clones Encoding an English Ivy Acyl Carrier Protein The BLASTX search using the EST sequences from clones listed in Table 5 revealed similarity of the polypeptide encoded by the cDNA to acyl carrier protein (ACP) from coriander (*Coriandrum sativum*) (Genbank Accession No. 5669599). Shown in Table 5 is the BLAST result for the ivy EST:

TABLE 5

BLAST Results for Sequences Encoding Polypeptides Homologous to Coriander Acyl Carrier Protein

| Clone | Status | BLAST pLog Score [gi 5669599] |
| --- | --- | --- |
| ehh1c.pk001.k9 | EST | 42.1% |
| ehh1c.pk001.k9:fis | FIS | 49.7% |

FIG. 2 presents an alignment of the amino acid sequences set forth in SEQ ID NO:4 and the *Coriandrum sativum* ACP sequence (SEQ ID NO:6). The data in Table 6 represents a calculation of the percent identity of the amino acid sequences set forth in SEQ ID NO:4 and the *Coriandrum sativum* ACP sequence (SEQ ID NO:6).

TABLE 6

Percent Identity of Amino Acid Sequences Deduced From the Nucleotide Sequences of cDNA Clones Encoding Polypeptides Homologous to Coriander Acyl Carrier Protein

| SEQ ID NO. | Percent Identity to [gi 5669599] |
| --- | --- |
| 4 | 65.8% |
| 6 | 74.5% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignment, BLAST score, and probabilities indicate that the nucleic acid fragment comprising the instant cDNA clone encodes a substantial portion of an ACP. These sequences represent examples of diverged ACP isoforms. Coriander accumulates significant quantities of petroselinic acid in its seeds. It is believed that the similarity between this English ivy ACP and the coriander protein is the result of their shared ability to produce petroselinic acid.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 m in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987)

*Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 8

Expression of a Diverged Acyl-ACP Desaturase from Hedera helix in Tobacco Cells

The Hedera helix EST ehh1c.pk002.f22 corresponds to a cDNA that encodes a diverged acyl—acyl carrier protein (ACP) desaturase. To determine the function of this polypeptide, the cDNA corresponding to EST ehh1c.pk002.f22 was expressed in tobacco callus under control of the cauliflower mosaic virus 35S promoter. The open-reading frame of the acyl-ACP desaturase cDNA was amplified by PCR to generate flanking 5' XbaI and 3' SstI restriction enzyme sites for cloning into the plant expression vector. The sequence of the sense oligonucleotide used in the amplification reaction was 5'-attctagaAGAAGAAATG-GCTTTGAAGC-3' (SEQ ID NO:11), and the sequence of the antisense oligonucleotide was 5'-atgagctcCCTTCCTGT-TCATATCTTC-3' (SEQ ID NO:12). The bases in lower case define restriction sites (XbaI, 5'-tctaga-3'; and SstI, 5'-gagctc-3') and flanking sequence that were added, to the sequences homologous to the English ivy desaturase, to facilitate restriction enzyme digestion and directional cloning of the PCR fragment. The design of the PCR primers was based on the sequence of the cDNA forEST ehh1c.pk002.f22 shown in SEQ ID NO:2. Thirty cycles of PCR amplification were conducted in a 100 µl volume using Pfu polymerase (Stratagene) and 25 ng of pBluescript SK(−) containing the cDNA for EST ehh1c.pk002.f22. The product from this reaction was subcloned into pPCR-Script AMP (Stratagene). Following restriction digestion with XbaI and SstI, the PCR product was moved from pPCR-Script AMP into the corresponding sites of the plant expression vector pBI121 (Clontech). The vector pBI121 is used for constitutive expression of transgenes mediated by the cauliflower mosaic virus 35S promoter. This vector contains right and left border regions flanking the inserted gene fusion to facilitate stable *Agrobacterium*-mediated transformation of the host plant cell and also contains within the border regions a nopaline phosphotransferase II (NPTII) gene under control of the cauliflower mosaic virus 35S promoter to provide for selection of transformed plant cells by kanamycin resistance. The resulting construct containing the 35S promoter fused with the cDNA for EST ehh1c.pk002.f22 was transformed into *Agrobacterium tumefaciens* LBA4404 cells. Cultures derived from these cells were used for transformation of tobacco (*Nicotiana tabacum* cv. Xanthi) leave disks according to the protocol described by Rogers, S. G., Horsch, R. B., and Fraley, R. T. (1986) *Methods Enzymol.* 118: 627–648. Kanamycin resistant tobacco callus resulting from this transformation was used to assess the function of the diverged acyl-ACP desaturase corresponding to the cDNA for EST ehh1c.pk002.f22.

Expression of the cDNA for EST ehh1c.pk0002.f22 in the resulting kanamycin resistant tobacco callus was confirmed by PCR analysis using the oligonucleotides described above and template consisting of first-strand cDNA prepared from RNA extracted from the transgenic callus. To determine the in vivo activity of the diverged acyl-ACP desaturase encoded by the cDNA for EST ehh1 c.pk002.f22, the fatty acids composition of the transgenic tobacco callus was examined by gas chromatography. Fatty acid methyl esters were prepared by homogenization of the transgenic tobacco callus in 1% (w/v) sodium methoxide in methanol using methods described by Hitz et al. (1994) *Plant Physiol.* 105:635–641. The recovered fatty acid methyl esters were then analyzed using a Hewlett-Packard 6890 chromatograph fitted with an Omegawax 320 column (30 m×0.32 mm inner diameter; Supelco). The oven temperature was programmed from 220° C. (2 min hold) to 240° C. at a rate of 20° C./min. The transgenic tobacco callus expressing the diverged Hedera helix acyl-ACP desaturase was found to contain a hexadecenoic acid (16:1) isomer and a octadecenoic acid (18:1) isomer that were absent from untranformed callus. These two isomers each accounted for 2 to 5% (w/w) of the total fatty acids of the transgenic tobacco callus. Gas chromatography-mass spectrometry (GC-MS) was performed to determine the double bond positions of the novel 16:1 and 18:1 isomers. For these analyses, fatty acid methyl esters were converted to dimethyl disulfide derivatives using the method described by Yamamoto, K., Shibahara, A., Nakayama, T., Kajimoto, G. (1991) *Chem. Phys. Lipids* 60:39–50. Dimethyl disulfide derivatives were analyzed by GC-MS using a Hewlett Packard 6890 gas chromatograph interfaced with a Hewlett Packard 5973 mass selective detector. Samples were resolved with a HP-INNOWax column (Hewlett Packard) (30 m×0.25 mm inner diameter), and the oven temperature was programmed from 185° C. (5 min hold) to 237° C. at a rate of 7.5° C./min. The resulting mass spectrum of the dimethyl disulfide derivative of the novel 16:1 methyl ester contained diagnostic ions consistent with that of a $\Delta^4$ isomer. In addition, the mass spectrum of the dimethyl disulfide derivative of the novel 18:1 methyl ester in the transgenic tobacco callus contained diagnostic ions consistent with that of petroselinic acid, the $18:1\Delta^6$ isomer. These results thus indicate that the diverged acyl-ACP desaturase corresponding to the cDNA for EST ehh1c.pk002.f22 is associated with petroselinic acid synthesis. Based on the biosynthetic pathway for petroselinic acid previously described in Umbelliferae species [Cahoon, E. B. and Ohlrogge, J. B. (1994) *Plant Physiol.* 104:827–844], the Hedera helix diverged acyl-ACP desaturase is likely a $\Delta^4$-specific palmitoyl (16:0)-ACP desaturase. This is consistent with the presence of the novel $16:1\Delta^4$ isomer in the transgenic tobacco callus. The $16:1\Delta^4$ isomer bound to ACP likely serves as the biosynthetic precursor for petroselinic acid ($18:1\Delta^6$), as described in Umbelliferae species [Cahoon, E. B. and Ohlrogge, J. B. (1994) *Plant Physiol.* 104:827–844].

What is claimed is:

1. An isolated polynucleotide comprising:
   (a) a nucleotide sequence encoding a polypeptide having $\Delta^4$-16:0-ACP desaturase activity, wherein the amino acid sequence of the polypeptide and the amino acid sequence of SEQ ID NO:2 have at least 95% sequence identity based on the Clustal alignment method, or
   (b) the complement of the nucleotide sequence of (a).

2. The polynucleotide of claim 1, wherein the amino acid sequence of the polypeptide comprises the amino acid sequence of SEQ ID NO:2.

3. The polynucleotide of claim 1 wherein the nucleotide sequence comprises the nucleotide sequence of SEQ ID NO:1.

4. An isolated nucleic acid molecule comprising:
   (a) at least 300 nucleotides and
   (b) said isolated nucleic acid molecule remains hybridized to an isolated polynucleotide comprising:
      (i) a nucleotide sequence encoding a polypeptide having Δ4-16:0-ACP desaturase activity, said nucleotide sequence comprising the nucleotide sequence of SEQ ID NO:1, or
      (ii) the complement of the nucleotide sequence of (i), under a wash condition of 0.1×SSC, 0.1% SDS, and 65° C.

5. A vector comprising the polynucleotide of claim 1.

6. A chimeric gene comprising the polynucleotide of claim 1 operably linked to at least one regulatory sequence.

7. A method for transforming a cell, comprising transforming a cell with the polynucleotide of claim 1.

8. A cell comprising the chimeric gene of claim 6.

9. A method for producing a plant comprising transforming a plant cell with the polynucleotide of claim 1 and regenerating a plant from the transformed plant cell.

10. A plant comprising the chimeric gene of claim 6.

11. A seed comprising the chimeric gene of claim 6.

12. A method for production of a polypeptide having $\Delta^4$-16:0-ACP desaturase activity comprising the steps of cultivating the cell of claim 8 under conditions that allow for the synthesis of the polypeptide and isolating the polypeptide from the cultivated cells, from the culture medium, or from both the cultivated cells and the culture medium.

13. A method for altering the level of $\Delta^4$-16:0-ACP desaturase expression in a host cell, the method comprising:
   (a) transforming a host cell with the chimeric gene of claim 6; and
   (b) growing the transformed cell in step (a) under conditions suitable for the expression of the chimeric gene.

14. A method for producing petroselinic acid in a plant, the method comprising:
   (a) transforming a plant with a chimeric gene comprising the isolated polynucleotide of claim 1 operably linked to at least one suitable regulatory sequence;
   (b) growing the transformed plant under conditions suitable for the expression of the chimeric gene; and
   (c) selecting those transformed plants producing petroselinic acid.

15. A method for producing seed oil containing fatty acids having petroselinic acid in the seeds of plants which comprises:
   (a) transforming a plant with a chimeric gene comprising the isolated nucleic acid fragment of claim 1 operably linked to at least one suitable regulatory sequence;
   (b) growing a fertile mature plant from the transformed plant cell of step (a);
   (c) screening progeny seeds from the fertile plants of step (b) for altered levels of acetylenic fatty acids; and
   (d) processing the progeny seed of step (c) to obtain seed oil containing petroselinic acid.

* * * * *

SEQUENCE LISTING

<160> NUMBER OF SEQ ID NOS: 12

<210> SEQ ID NO 1
<211> LENGTH: 1344
<212> TYPE: DNA
<213> ORGANISM: Hedera helix
<220> FEATURE:
<221> NAME/KEY: unsure
<222> LOCATION: (997)

<400> SEQUENCE: 1

```
caacccaga aataaaaat aaaaactcaa gaagaagaag aagaaatggc tttgaagctc    60
aatttccaat gcaagaagaa ccaccctgct gcgtttgcta agtcaccatt accagtgacc   120
agagttagct ctccaagggt tttcatggct tccactgtca actctaactc catggttctt   180
gataatctca aaagtccgcc aaatcttcaa gtcactcact ctatgccacc ccaaaagcta   240
gaaatattca agtcccttga tgattgggct aggaacaatg tgttgattca cctcaaatct   300
gtcgagaaat cttggcaacc acaagactac ttgccggatc cggtgtcaga cggattcgag   360
gagcaagtgc gggagttgag ggaaagggcc aaggagattc ccgacgacta ttttgtggtg   420
ttagttggag atatgatcac agaagaagca cttccaacat atatgtctat gctcaatagg   480
tgtgatggta ttaaggatga gactgggggct gagcccagtg cttgggcaat gtggactagg   540
gcatggactg ccgaagagaa tagacatggt gaccttctca ataagtacct ttatttgtct   600
ggaagggttg atatgaggaa aattgagaag actattcaat atctcatcgg ctcaggaatg   660
gatatcaagt cagaaaacag cccctaccta ggcttcatct acacatcctt ccaagagaga   720
gcaaccttca tatcccatgc caacacagcc aagctggccc aacactacgg cgacaagaac   780
ctcgctcaca tctgcggctc catcgcctcc gacgagaagc gccacgccac agcctacacc   840
aagatcgtgg aaaagctcgc tgagatcgac cccgacacaa cagtaattgc ttttgcagat   900
atgatgcgca aaaaaataac aatgccacgc cacttgatgt acgacggaag tgacgaactt   960 cttttaaac atttcacggc ggttgctcag agagtgnggg tttattctgc gttggattat  1020
tgcgacatct tagagtttct ggtggataaa tggaatgtgg aaaggcttac ggggctgtcg  1080 gacgagggc gaaaagcgca ggaatatgtg tgtgaattgg gtcccaagat taggcgagtg  1140
gaagagaaag tgcaggggaa ggagaagaag aagaaagctg agcaccctgt ttctttcagc  1200
tggattttca atcgggagtt gaagatatga acaggaaggg aagggaatgg aggagcaaat  1260
gagtgtagta gatttctata tgcatgttta tatattatga atgattatta tataataata  1320
```
agtgtttgag ttttaagtaa aaaa                                           1344

<210> SEQ ID NO 2
<211> LENGTH: 394
<212> TYPE: PRT
<213> ORGANISM: Hedera helix
<220> FEATURE:
<221> NAME/KEY: UNSURE
<222> LOCATION: (318)

<400> SEQUENCE: 2

```
Met ala Leu Lys Leu Asn Phe Gln Cys Lys Lys Asn His Pro Ala Ala
 1               5                  10                  15

Phe Ala Lys Ser Pro Leu Pro Val Thr Arg Val Ser Ser Pro Arg Val
             20                  25                  30

Phe Met Ala Ser Thr Val Asn Ser Asn Ser Met Val Leu Asp Asn Leu
         35                  40                  45

Lys Ser Pro Pro Asn Leu Gln Val Thr His Ser Met Pro Pro Gln Lys
     50                  55                  60

Leu Glu Ile Phe Lys Ser Leu Asp Asp Trp Ala Arg Asn Asn Val Leu
 65                  70                  75                  80

Ile His Leu Lys Ser Val Glu Lys Ser Trp Gln Pro Gln Asp Tyr Leu
                 85                  90                  95

Pro Asp Pro Val Ser Asp Gly Phe Glu Gln Val Arg Glu Leu Arg
            100                 105                 110

Glu Arg Ala Lys Glu Ile Pro Asp Asp Tyr Phe Val Val Leu Val Gly
            115                 120                 125

Asp Met Ile Thr Glu Glu Ala Leu Pro Thr Tyr Met Ser Met Leu Asn
    130                 135                 140

Arg Cys Asp Gly Ile Lys Asp Glu Thr Gly Ala Glu Pro Ser Ala Trp
145                 150                 155                 160

Ala Met Trp Thr Arg Ala Trp Thr Ala Glu Asn Arg His Gly Asp
                165                 170                 175

Leu Leu Asn Lys Tyr Leu Tyr Leu Ser Gly Arg Val Asp Met Arg Lys
            180                 185                 190

Ile Glu Lys Thr Ile Gln Tyr Leu Ile Gly Ser Gly Met Asp Ile Lys
            195                 200                 205

Ser Glu Asn Ser Pro Tyr Leu Gly Phe Ile Tyr Thr Ser Phe Gln Glu
    210                 215                 220

Arg Ala Thr Phe Ile Ser His Ala Asn Thr Ala Lys Leu Ala Gln His
225                 230                 235                 240

Tyr Gly Asp Lys Asn Leu Ala His Ile Cys Gly Ser Ile Ala Ser Asp
                245                 250                 255

Glu Lys Arg His Ala Thr Ala Tyr Thr Lys Ile Val Glu Lys Leu Ala
            260                 265                 270

Glu Ile Asp Pro Asp Thr Thr Val Ile Ala Phe Ala Asp Met Met Arg
            275                 280                 285

Lys Lys Ile Thr Met Pro Ala His Leu Met Tyr Asp Gly Ser Asp Glu
    290                 295                 300

Leu Leu Phe Lys His Phe Thr Ala Val Ala Gln Arg Val Xaa Val Tyr
305                 310                 315                 320

Ser Ala Leu Asp Tyr Cys Asp Ile Leu Glu Phe Leu Val Asp Lys Trp
                325                 330                 335

Asn Val Glu Arg Leu Thr Gly Leu Ser Asp Glu Gly Arg Lys Ala Gln
            340                 345                 350
```

```
Glu Tyr Val Cys Glu Leu Gly Pro Lys Ile Arg Arg Val Glu Glu Lys
            355                 360                 365

Val Gln Gly Lys Glu Lys Lys Lys Ala Glu His Pro Val Ser Phe
    370                 375                 380

Ser Trp Ile Phe Asn Arg Glu Leu Lys Ile
385                 390
```

```
<210> SEQ ID NO 3
<211> LENGTH: 445
<212> TYPE: DNA
<213> ORGANISM: Hedera helix

<400> SEQUENCE: 3
cttcgtgctc tccgcctctt gttttttct ctttccaaat attttctgag taattttctc      60
agatctattc ctctttcttc tctccctaat ttgatccatc aatggcttct gttactgcct    120
catcgatttc cttcacctct atcgcaagct ccctcaagca aaaccaggga cttgccaaga    180
gttcaatttc actctctgtc aatgggaaat ccttccgttc acttaggttg ctgtcggcac    240
cacttcgctt cagagtgtca tgcgcagcga aaccagcgac agtggacaag gtgtgtgaga    300
ttgtgcggaa acaactggcg ctgccgctga ttctgcaagt cactggagag tcaaaattcg    360
cagcgcttgg ggctgattct ctcgacacgg ttgagattgt gatgggacta aaggaggaat    420
tcggaatcaa gcgtgggaaa aagaa                                          445
```

```
<210> SEQ ID NO 4
<211> LENGTH: 114
<212> TYPE: PRT
<213> ORGANISM: Hedera helix

<400> SEQUENCE: 4

Met Ala Ser Val Thr Ala Ser Ser Ile Ser Phe Thr Ser Ile Ala Ser
  1               5                  10                  15

Ser Leu Lys Gln Asn Gln Gly Leu Ala Lys Ser Ser Ile Ser Leu Ser
             20                  25                  30

Val Asn Gly Lys Ser Phe Arg Ser Leu Arg Leu Leu Ser Ala Pro Leu
         35                  40                  45

Arg Phe Arg Val Ser Cys Ala Ala Lys Pro Ala Thr Val Asp Lys Val
     50                  55                  60

Cys Glu Ile Val Arg Lys Gln Leu Ala Leu Pro Leu Ile Leu Gln Val
 65                  70                  75                  80

Thr Gly Glu Ser Lys Phe Ala Ala Leu Gly Ala Asp Ser Leu Asp Thr
                 85                  90                  95

Val Glu Ile Val Met Gly Leu Glu Glu Phe Gly Ile Lys Arg Gly
            100                 105                 110

Lys Lys
   114
```

```
<210> SEQ ID NO 5
<211> LENGTH: 920
<212> TYPE: DNA
<213> ORGANISM: Hedera helix

<400> SEQUENCE: 5
cttcgtgctc tccgcctctt gttttttct ctttccaaat attttctgag taattttctc      60
agatctattc ctctttcttc tctccctaat ttgatccatc aatggcttct gttactgcct    120
catcgatttc cttcacctct atcgcaagct ccctcaagca aaaccaggga cttgccaaga    180
```

```
gttcaatttc actctctgtc aatgggaaat ccttccgttc acttaggttg ctgtcggcac    240
cacttcgctt cagagtgtca tgcgcagcga aaccagcgac agtggacaag gtgtgtgaga    300
ttgtgcggaa acaactggcg ctgccggctg attctgcagt cactggagag tcaaaattcg    360
cagcgcttgg ggctgattct ctcgacacgg ttgagattgt gatgggacta gaggaggaat    420
tcggaatcag cgtggaagaa gaaagtgcac agaccattgc cactgttcaa gatgcagcgg    480
acctgattga gaagcttgtt gagaaaaagg agtagaagaa ccggggtaga aattctgcaa    540
aataggttta ttaaggacag ttactttatt aggatggttc atcaagatct tcattaccct    600
acatttattt gtatgctcct catgaagccg caaaagtagt agtggtgatg aaatttaccc    660
cgagtcttcg ccttaattat caagtgaga gagccagaaa aagaggctat gctatctctc    720
atctcgttat gttttatttt cttgtcggac ttctggttgg agtttttttt ttttatctaa    780
acatgatatt agtcttgttt aaagtttct caaaaaaata tatcttgttg ttgagactga    840
tggagttatt gctcttgata ttttgaatgt attttgagtt attcaaaaaa aaaaaaaaaa    900
aaaaaaaaaa aaaaaaaaaa                                                920
```

<210> SEQ ID NO 6
<211> LENGTH: 137
<212> TYPE: PRT
<213> ORGANISM: Hedera helix

<400> SEQUENCE: 6

```
Met Ala Ser Val Thr Ala Ser Ser Ile Ser Phe Thr Ser Ile Ala Ser
 1               5                  10                  15

Ser Leu Lys Gln Asn Gln Gly Leu Ala Lys Ser Ser Ile Ser Leu Ser
             20                  25                  30

Val Asn Gly Lys Ser Phe Arg Ser Leu Arg Leu Ser Ala Pro Leu
         35                  40                  45

Arg Phe Arg Val Ser Cys Ala Ala Lys Pro Ala Thr Val Asp Lys Val
     50                  55                  60

Cys Glu Ile Val Arg Lys Gln Leu Ala Leu Pro Ala Asp Ser Ala Val
 65                  70                  75                  80

Thr Gly Glu Ser Lys Phe Ala Ala Leu Gly Ala Asp Ser Leu Asp Thr
             85                  90                  95

Val Glu Ile Val Met Gly Leu Glu Glu Glu Phe Gly Ile Ser Val Glu
            100                 105                 110

Glu Glu Ser Ala Gln Thr Ile Ala Thr Val Gln Asp Ala Ala Asp Leu
        115                 120                 125

Ile Glu Lys Leu Val Glu Lys Lys Glu
    130                 135
```

<210> SEQ ID NO 7
<211> LENGTH: 385
<212> TYPE: PRT
<213> ORGANISM: Coriandrum sativum

<400> SEQUENCE: 7

```
Met Ala Met Lys Leu Asn Ala Leu Met Thr Leu Gln Cys Pro Lys Arg
 1               5                  10                  15

Asn Met Phe Thr Arg Ile Ala Pro Pro Gln Ala Gly Arg Val Arg Ser
             20                  25                  30

Lys Val Ser Met Ala Ser Thr Leu His Ala Ser Pro Leu Val Phe Asp
         35                  40                  45
```

-continued

```
Lys Leu Lys Ala Gly Arg Pro Glu Val Asp Glu Leu Phe Asn Ser Leu
 50                  55                  60

Glu Gly Trp Ala Arg Asp Asn Ile Leu Val His Leu Lys Ser Val Glu
 65                  70                  75                  80

Asn Ser Trp Gln Pro Gln Asp Tyr Leu Pro Asp Pro Thr Ser Asp Ala
                 85                  90                  95

Phe Glu Asp Gln Val Lys Glu Met Arg Glu Arg Ala Lys Asp Ile Pro
            100                 105                 110

Asp Glu Tyr Phe Val Val Leu Val Gly Asp Met Ile Thr Glu Glu Ala
        115                 120                 125

Leu Pro Thr Tyr Met Ser Met Leu Asn Arg Cys Asp Gly Ile Lys Asp
    130                 135                 140

Asp Thr Gly Ala Gln Pro Thr Ser Trp Ala Thr Trp Thr Arg Ala Trp
145                 150                 155                 160

Thr Ala Glu Glu Asn Arg His Gly Asp Leu Leu Asn Lys Tyr Leu Tyr
                165                 170                 175

Leu Ser Gly Arg Val Asp Met Arg Met Ile Glu Lys Thr Ile Gln Tyr
            180                 185                 190

Leu Ile Gly Ser Gly Met Asp Thr Lys Thr Glu Asn Cys Pro Tyr Met
        195                 200                 205

Gly Phe Ile Tyr Thr Ser Phe Gln Glu Arg Ala Thr Phe Ile Ser His
    210                 215                 220

Ala Asn Thr Ala Lys Leu Ala Gln His Tyr Gly Asp Lys Asn Leu Ala
225                 230                 235                 240

Gln Val Cys Gly Asn Ile Ala Ser Asp Glu Lys Arg His Ala Thr Ala
                245                 250                 255

Tyr Thr Lys Ile Val Glu Lys Leu Ala Glu Ile Asp Pro Asp Thr Thr
            260                 265                 270

Val Ile Ala Phe Ser Asp Met Met Arg Lys Lys Ile Gln Met Pro Ala
        275                 280                 285

His Ala Met Tyr Asp Gly Ser Asp Asp Met Leu Phe Lys His Phe Thr
    290                 295                 300

Ala Val Ala Gln Gln Ile Gly Val Tyr Ser Ala Trp Asp Tyr Cys Asp
305                 310                 315                 320

Ile Ile Asp Phe Leu Val Asp Lys Trp Asn Val Ala Lys Met Thr Gly
                325                 330                 335

Leu Ser Gly Glu Gly Arg Lys Ala Gln Glu Tyr Val Cys Ser Leu Ala
            340                 345                 350

Ala Lys Ile Arg Arg Val Glu Glu Lys Val Gln Gly Lys Glu Lys Lys
        355                 360                 365

Ala Val Leu Pro Val Ala Phe Ser Trp Ile Phe Asn Arg Gln Ile Ile
    370                 375                 380

Ile
385

<210> SEQ ID NO 8
<211> LENGTH: 137
<212> TYPE: PRT
<213> ORGANISM: Coriandrum sativum

<400> SEQUENCE: 8

Met Ala Ala Phe Thr Ala Ser Ser Val Ser Phe Thr Pro Leu Ser Ile
  1               5                  10                  15

Ser Leu Asn Gln Thr Lys Gly Phe Ala Arg Gly Ser Val Ser Ile Pro
             20                  25                  30
```

```
Ala Lys Ala Lys Ser Phe Gly Ala Leu Thr Leu Arg Asn Ala Pro Leu
         35                  40                  45

Arg Phe Arg Val Ser Cys Ala Ala Lys Pro Glu Thr Val Glu Lys Val
     50                  55                  60

Cys Glu Ile Val Lys Lys Gln Leu Ala Leu Pro Pro Thr Thr Glu Val
 65                  70                  75                  80

Ser Gly Asp Ser Lys Phe Ala Ala Leu Gly Ala Asp Ser Leu Asp Thr
                 85                  90                  95

Val Glu Ile Val Met Gly Leu Glu Glu Glu Phe Gly Ile Ser Val Glu
             100                 105                 110

Glu Glu Ser Ala Gln Ala Ile Ala Thr Val Gln Asp Ala Ala Asp Leu
         115                 120                 125

Ile Glu Lys Leu Cys Glu Lys Lys Glu
         130                 135
```

<210> SEQ ID NO 9
<211> LENGTH: 1381
<212> TYPE: DNA
<213> ORGANISM: Hedera helix

<400> SEQUENCE: 9

```
ctttttctct ctcttccttg cagaattaat ccggtggaaa ttacaaaatc aaaccagaaa       60
ataaaaataa aaactcaaga agaagaagaa gaaatggctt tgaagctcaa tttccaatgc      120
aagaagaacc accctgctgc gtttgctaag tcaccattac cagtgaccag agttagctct      180
ccaagggttt tcatggcttc cactgtcaac tctaactcca tggttcttga taatctcaaa      240
agtcctccaa atcttcaagt cactcactct atgccacccc aaaagctaga atatattcaag     300
tcccttgatg attgggctag aacaatgtgt tgattcacc tcaaatctgt cgagaaatct       360
tggcaaccac aagactactt gccggatccg gtgtcagacg gattcgagga gcaagtgcgg      420
gagttgaggg aaagggccaa ggagattccc gacgactatt ttgtggtgtt agttggagat      480
atgatcacag aagaagcact tccaacatat atgtctatgc tcaataggtg tgatggtatt      540
aaggatgaga ctggggctga gcccagtgct tgggcaatgt ggactagggc atggactgcc      600
gaagagaata gacatggtga ccttctcaat aagtaccttt atttgtctgg aagggttgat      660
atgaggaaaa ttgagaagac tattcaatat ctcatcggct caggaatgga tatcaagtca      720
gaaaacagcc cctacctagg cttcatctac acatccttcc aagagagagc aaccttcata      780
tcccatgcca acacagccaa gctggcccaa cactacggcg acaagaacct cgctcacatc      840
tgcggctcca tcgcctccga cgagaagcgc cacgccacag cctacaccaa gatcgtggaa      900
aagctcgctg agatcgaccc cgacacaaca gtaattgctt ttgcagatat gatgcgcaaa      960
aaataacaa tgccagcgca cttgatgtac gacggaagtg acgaacttct ttttaaacat     1020
ttcacggcgg ttgctcagag agtggggggtt tattctgcgt tggattattg cgacatctta    1080
gagtttctgg tggataaatg gaatgtggaa aggcttacgg ggctgtcgga cgaggggcga     1140
aaagcgcagg aatatgtgtg tgaattgggt cccaagatta ggcgagtgga agagaaagtg     1200
caggggaagg agaagaagaa gaaagctgag caccctgttt ctttcagctg gatttcaat     1260
cgggagttga agatatgaac aggaagggaa gggaatggag gagcaaatga gtgtagtaga     1320
tttctatatg catgtttata tattatgaat gattattata taataataag tgtttgagtt     1380
t                                                                    1381
```

```
<210> SEQ ID NO 10
<211> LENGTH: 394
<212> TYPE: PRT
<213> ORGANISM: Hedera helix

<400> SEQUENCE: 10

Met Ala Leu Lys Leu Asn Phe Gln Cys Lys Lys Asn His Pro Ala Ala
 1               5                  10                  15

Phe Ala Lys Ser Pro Leu Pro Val Thr Arg Val Ser Ser Pro Arg Val
                20                  25                  30

Phe Met Ala Ser Thr Val Asn Ser Asn Ser Met Val Leu Asp Asn Leu
            35                  40                  45

Lys Ser Pro Pro Asn Leu Gln Val Thr His Ser Met Pro Pro Gln Lys
        50                  55                  60

Leu Glu Ile Phe Lys Ser Leu Asp Asp Trp Ala Arg Asn Asn Val Leu
 65                  70                  75                  80

Ile His Leu Lys Ser Val Glu Lys Ser Trp Gln Pro Gln Asp Tyr Leu
                85                  90                  95

Pro Asp Pro Val Ser Asp Gly Phe Glu Glu Gln Val Arg Glu Leu Arg
                100                 105                 110

Glu Arg Ala Lys Glu Ile Pro Asp Asp Tyr Phe Val Val Leu Val Gly
            115                 120                 125

Asp Met Ile Thr Glu Glu Ala Leu Pro Thr Tyr Met Ser Met Leu Asn
        130                 135                 140

Arg Cys Asp Gly Ile Lys Asp Glu Thr Gly Ala Glu Pro Ser Ala Trp
145                 150                 155                 160

Ala Met Trp Thr Arg Ala Trp Thr Ala Glu Glu Asn Arg His Gly Asp
                165                 170                 175

Leu Leu Asn Lys Tyr Leu Tyr Leu Ser Gly Arg Val Asp Met Arg Lys
            180                 185                 190

Ile Glu Lys Thr Ile Gln Tyr Leu Ile Gly Ser Gly Met Asp Ile Lys
        195                 200                 205

Ser Glu Asn Ser Pro Tyr Leu Gly Phe Ile Tyr Thr Ser Phe Gln Glu
    210                 215                 220

Arg Ala Thr Phe Ile Ser His Ala Asn Thr Ala Lys Leu Ala Gln His
225                 230                 235                 240

Tyr Gly Asp Lys Asn Leu Ala His Ile Cys Gly Ser Ile Ala Ser Asp
                245                 250                 255

Glu Lys Arg His Ala Thr Ala Tyr Thr Lys Ile Val Glu Lys Leu Ala
            260                 265                 270

Glu Ile Asp Pro Asp Thr Thr Val Ile Ala Phe Ala Asp Met Met Arg
        275                 280                 285

Lys Lys Ile Thr Met Pro Ala His Leu Met Tyr Asp Gly Ser Asp Glu
    290                 295                 300

Leu Leu Phe Lys His Phe Thr Ala Val Ala Gln Arg Val Gly Val Tyr
305                 310                 315                 320

Ser Ala Leu Asp Tyr Cys Asp Ile Leu Glu Phe Leu Val Asp Lys Trp
                325                 330                 335

Asn Val Glu Arg Leu Thr Gly Leu Ser Asp Glu Gly Arg Lys Ala Gln
            340                 345                 350

Glu Tyr Val Cys Glu Leu Gly Pro Lys Ile Arg Arg Val Glu Glu Lys
        355                 360                 365

Val Gln Gly Lys Glu Lys Lys Lys Ala Glu His Pro Val Ser Phe
    370                 375                 380
```

```
Ser Trp Ile Phe Asn Arg Glu Leu Lys Ile
385                 390

<210> SEQ ID NO 11
<211> LENGTH: 28
<212> TYPE: DNA
<213> ORGANISM: Artificial Sequence
<220> FEATURE:
<223> OTHER INFORMATION: PCR primer

<400> SEQUENCE: 11
attctagaag aagaaatggc tttgaagc                                    28

<210> SEQ ID NO 12
<211> LENGTH: 27
<212> TYPE: DNA
<213> ORGANISM: Artificial Sequence
<220> FEATURE:
<223> OTHER INFORMATION: PCR primer

<400> SEQUENCE: 12
atgagctccc ttcctgttca tatcttc                                     27
```